United States Patent [19]

Kanbara

[11] Patent Number: 4,805,595
[45] Date of Patent: Feb. 21, 1989

[54] FLEXIBLE TUBE ASSEMBLY FOR ENDOSCOPE

[75] Inventor: Koji Kanbara, Tokyo, Japan

[73] Assignee: Olympus Optical Co., Ltd., Tokyo, Japan

[21] Appl. No.: 184,289

[22] Filed: Apr. 21, 1988

[30] Foreign Application Priority Data

Apr. 28, 1987 [JP] Japan .................. 62-103250

[51] Int. Cl.$^4$ .............................................. A61B 1/00
[52] U.S. Cl. ...................................................... 128/4
[58] Field of Search .................... 128/4, 6; 138/120

[56] References Cited

U.S. PATENT DOCUMENTS

| | | |
|---|---|---|
| 779,374 | 1/1905 | Phillips . |
| 3,670,721 | 6/1972 | Fukami et al. ............... 128/6 |
| 4,327,711 | 5/1982 | Takagi .......................... 128/4 |
| 4,329,980 | 5/1982 | Terada .......................... 128/4 |
| 4,669,172 | 6/1987 | Petruzzi ...................... 28/6 X |
| 4,753,222 | 6/1988 | Morishita ..................... 128/4 |

FOREIGN PATENT DOCUMENTS 60-187701 5/1984 Japan .
59-190201 12/1984 Japan .

Primary Examiner—William H. Grieb
Attorney, Agent, or Firm—Ladas & Parry

[57] ABSTRACT

A flexible tube assembly for an endoscope has outer diameter D and includes a helical tube constituted by a helically wound belt-like member having width l and thickness t. The helical tube has inner diameter d, and gaps s are formed between adjacent coils of the belt-like member of the helical tube. Gap s satisfies the following inequality:

$$3 \geq s \geq l\,(d/2+t)/(30+D/2-d/2-t) \text{ (mm)}$$

A net tube covers the outer surface of the helical tube. An outer sheath covers the outer surface of the net tube.

6 Claims, 4 Drawing Sheets

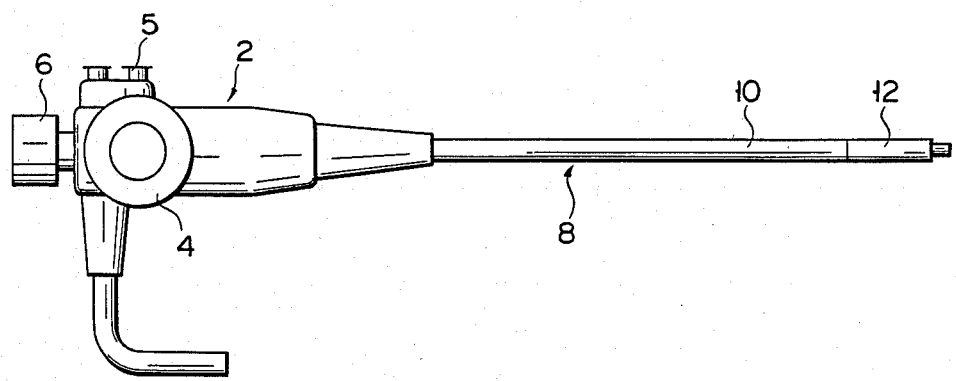
F I G. 1
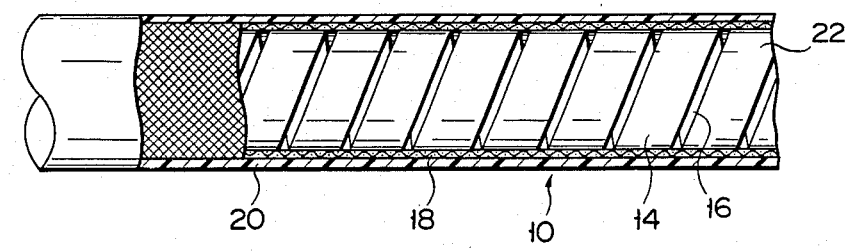
F I G. 2

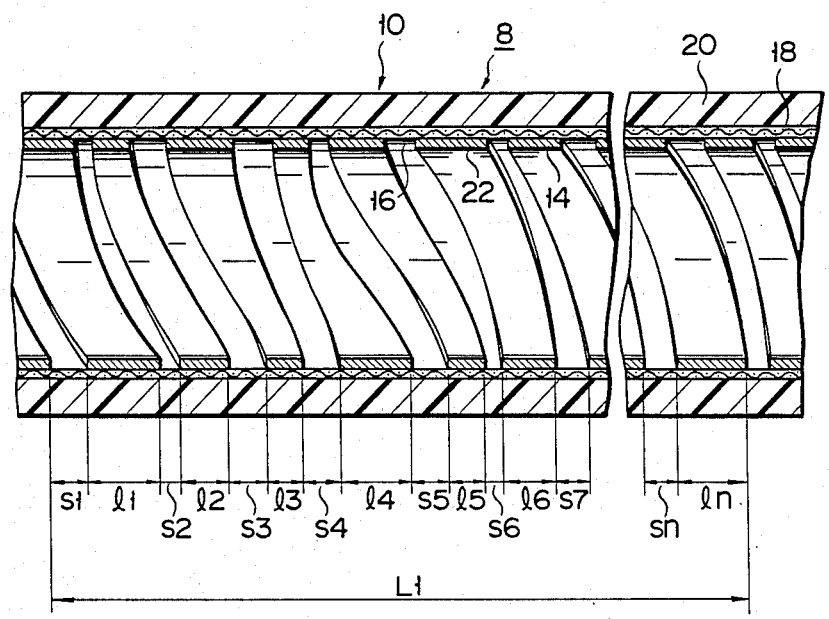
F I G. 8
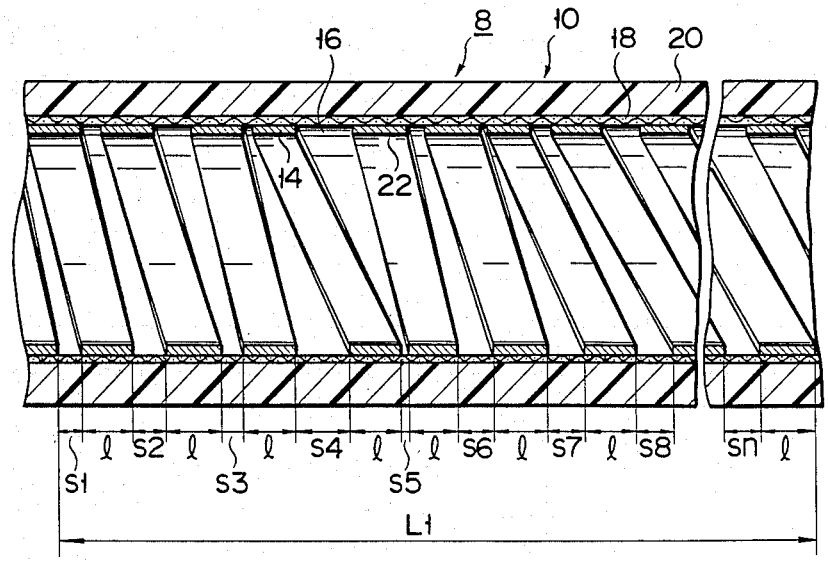
F I G. 9

FLEXIBLE TUBE ASSEMBLY FOR ENDOSCOPE

BACKGROUND OF THE INVENTION

1. Field of the Invention

The present invention relates to a flexible tube assembly for an endoscope, which constitutes a body of an insertion portion of the endoscope.

2. Description of the Related Art

A typical endoscope is disclosed in, e.g., Japanese Utility Model Disclosure Nos. 59-190201 and 60-187701. This endoscope comprises operation and insertion sections. An angle knob for operating a bending portion of the insertion section, an eyepiece for observation, and other operation means are mounted on the operation section.

A body of the insertion section is constituted by a flexible tube assembly. Light and image guides, a forceps channel tube, and the like are stored in the flexible tube assembly. An operator can observe a portion in front of the distal end of the insertion section through the image guide connected to the eyepiece.

The bending portion arranged on the distal end of the insertion section can be bent in a desired direction upon operation of the angle knob. For this reason, the operator can observe a desired portion in a body cavity using this endoscope.

A helical tube is arranged at an innermost portion of the flexible tube assembly so as to prevent the flexible tube assembly from being collapsed by an external force. This helical tube is constituted by a belt-like plate coiled in a helical shape with gaps. A net tube covers the outer surface of the helical tube to prevent its twisting. In addition, the outer surface of the net tube is covered with an outer sheath formed of a thermoplastic elastomer.

When the insertion section of the endoscope having the above-described arrangement is inserted into a body cavity, the insertion section is bent in accordance with the shape of the body cavity. In this case, a side wall of a curvature center side of the bent flexible tube assembly is contracted, whereas a side wall on the opposite side is expanded. At the same time, gaps are reduced on the curvature center side and are widened on the opposite side.

When the insertion portion of the endoscope is inserted into, e.g., the duodenum of a patient, it is bent at a relatively small radius of curvature. For this reason, especially in such a case, a flexible tube assembly which can be bent at a small radius of curvature is required.

When an insertion section of an endoscope having a typical flexible tube assembly is inserted into, e.g., the duodenum of a patient, before the insertion section is bent along the shape of the duodenum, gaps on one side of a helical tube disappear and hence the insertion section cannot be sufficiently bent. This may cause a pain to the patient, or distort the helical tube and damage image and light guides, and the like stored therein. Furthermore, the overall flexible tube assembly may be disabled.

If the gaps of the helical tube are excessively expanded in order to solve such a problem, a net tube may be pinched in the gaps and damaged.

SUMMARY OF THE INVENTION

It is an object of the present invention to provide a flexible tube assembly for an endoscope, which can be bent without causing a net tube to be pinched in gaps of a helical tube, and can be bent along the shape of a body cavity such as a duodenum at a relatively small radius of curvature.

The object of the present invention is achieved by the following flexible tube assembly. The flexible tube assembly of this endoscope has outer diameter D and comprises a helical tube constituted by a helically wound belt-like member having width l and thickness t. This helical tube has inner diameter d. Gap s is formed between adjacent coils of the belt-like member and satisfies the following inequality:

$$3 \geq s \geq l(d/2+t)/(30+D/2-d/2-l) \text{ (mm)}$$

In addition, the outer surface of the helical tube is covered with a net tube and the outer surface thereof is covered with an outer sheath.

The flexible tube assembly according to the present invention formed such that when the outer diameter of the assembly is set to be D, and the width, the gap, and the inner diameter of the helical tube are respectively set to be l, s, and d, gap s satisfies the following inequality:

$$3 \geq s \geq l(d/2+t)/(30+D/2-d/2-l) \text{ (mm)}$$

Therefore, the radius of an inscribed circle upon bending of the flexible tube assembly can be reduced to 30 mm or less. When an insertion section of the endoscope having this flexible tube assembly is inserted into a body cavity, a pain experienced by a patient can be reduced. In addition, various mechanisms stored in the flexible tube assembly are free from damages when the insertion section is bent at a relatively small radius of curvature, and hence durability of the endoscope can be improved.

BRIEF DESCRIPTION OF THE DRAWINGS

FIG. 1 is a side view of an endoscope as a whole;

FIG. 2 is a partial sectional view of an insertion section of the endoscope;

FIG. 8 is a longitudinal sectional view of a flexible tube assembly according to the third embodiment of the present invention; and FIG. 9 is a longitudinal sectional view of a flexible tube assembly according to a fourth embodiment of the present invention.

DETAILED DESCRIPTION OF THE PREFERRED EMBODIMENTS

Figure 3:
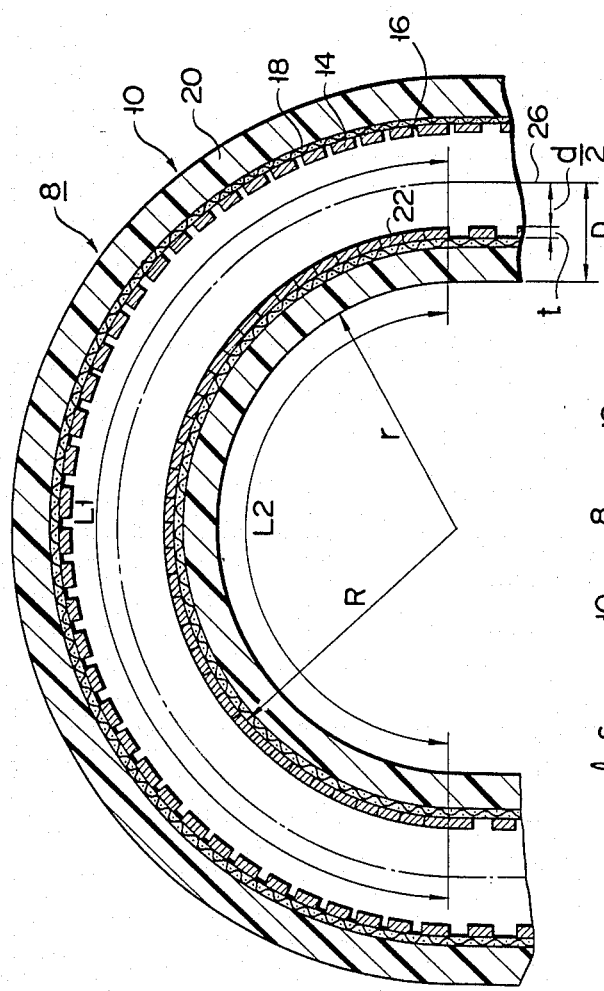
FIGS. 3 and 4 are longitudinal sectional views of a flexible tube assembly according to a first embodiment of the present invention.

The embodiments of the present invention will be described below with reference to the accompanying drawings.

An endoscope shown in FIG. 1 comprises operation section 2 and insertion section 8. Angle knob 4, operation switch 5, and eyepiece 6 are mounted on operation section 2. The body of insertion section 8 is constituted by flexible tube assembly 10. Bending portion 12 is connected to the distal end of flexible tube assembly 10. Angle knob 4 serves to operate bending portion 12 by bending it. As shown in FIG. 2, helical tube 14 is disposed inside flexible tube assembly 10 so as to prevent flexible tube assembly 10 from collapsing due to external force. Light and image guides and a channel tube (all of which are not shown) are stored in the inner space of helical tube 14. Helical tube 14 is constituted by helically wound belt-like plate 22 with gaps 16. The outer surface of helical tube 14 is covered with net tube 18 to prevent flexible tube assembly 10 from twisting. In addition, the outer surface of net tube 18 is covered with outer sheath 20 formed of a thermoplastic elastomer.

A flexible tube assembly according to a first embodiment of the present invention will be described with reference to FIGS. 3 and 4.

As shown in FIG. 3, insertion section 8 of the endoscope comprises flexible tube assembly 10. Helical tube 14 is arranged at an innermost portion of flexible tube assembly 10. Net tube 18 covers the outer surface of helical tube 14. In addition, the outer surface of net tube 18 is covered with outer sheath 20 formed of a thermoplastic elastomer.

Helical tube 14 is constituted by belt-like plate 22 composed of a metal or plastic wound in a helical shape. That is, helical tube 14 is formed by helically winding belt-like plate 22 having a predetermined width along the axial direction of flexible tube assembly 10. The coil widths of belt-like plate 22 constituting helical tube 14 and each gap 16 between the coils of beltlike plate 22 are respectively set to be l and s.

Assuming that the thickness of belt-like plate 22 is t, the inner diameter of flexible tube assembly 10 is d, i.e., the inner diameter defined by helical tube 14 is d, and the outer diameter of flexible tube assembly 10 is D, i.e., the outer diameter defined by outer sheath 20 is D, flexible tube assembly 10 is formed so as to have gap s satisfying the following inequality:

$$3 \geq s \geq l(d/2+t)/(30+D/2-d/2-t) \text{ unit: mm} \quad (1)$$

More specifically, when flexible tube assembly 10 shown in FIG. 3 is bent at inradius r=30 mm to be formed into a semicircular shape, length L1 of a central line of flexible tube assembly 10 is given as:

$$L1 = 2 \times \pi \times (30 + D/2) \times \tfrac{1}{2} \quad (2)$$

$$= \pi(30 + D/2) \quad (3)$$

Figure 4:
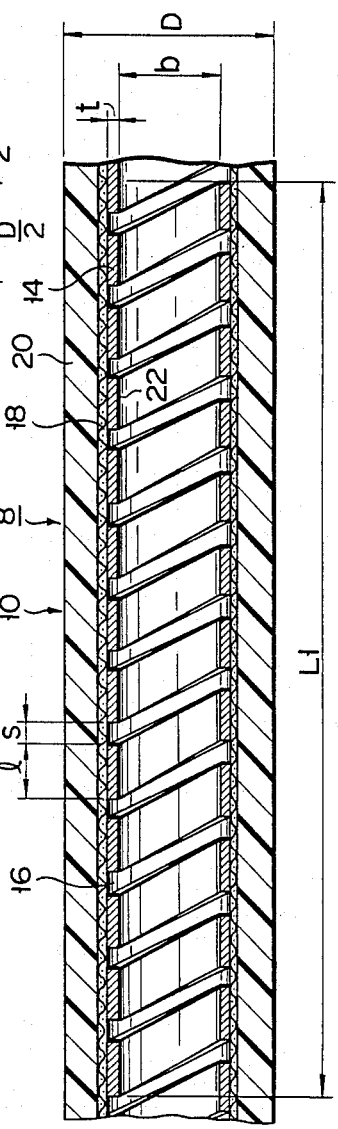

When flexible tube assembly 10 is in a linear state as shown in FIG. 4, number n of plate coils having widths l of helical tube 14 present within length L1 can be given as:

$$n = L1/(l+s) \quad (4)$$

When L1 represented by equation (3) is substituted for L1 in equation (4), $$n = \pi(30+D/2)/(l+s) \quad (5)$$

When flexible tube assembly 10 is bent at inradius r=30 mm to be formed into a semicircle, inradius R of the outer surface of helical tube 14 located inside central line 26 of flexible tube assembly 10 is given as:

$$R = 30 + D/2 - d/2 - t \quad (6)$$

Length L2 of an arc constituting the semicircle with radius R in the axial direction is given as:

$$L2 = 2 \cdot \pi \cdot R \times \tfrac{1}{2} \quad (7)$$

When R represented by equation (6) is substituted for R in equation (7), $$L2 = \pi(30 + D/2 - d/2 - t) \quad (8)$$

If width l is to be present within length L2 while inequality of $s \geq 0$ is satisfied, the following inequality must be satisfied:

$$L2 \geq ln \quad (9)$$

Then, $$\pi(30+D/2-d/2-t) \geq l \times \pi(30+D/2)/(l+s) \quad (10)$$

In addition, s can be given as:
$$s \geq l(d/2+t)/(30+D/2-d/2-t) \quad (11)$$

When each gap s is set to be 3 mm or more, a corresponding portion of net tube 18 is inserted in gap s upon the bending of flexible tube assembly 10. Therefore, $3 \geq s$ (mm) must be satisfied.

Consequently, the following inequality must be satisfied:

$$3 \geq s \geq l(d/2+t)/(30+D/2-d/2-t) \quad (1)$$

Furthermore, width l is preferably set to be 1 to 5 mm so as to obtain a strength for maintaining the shape of helical tube 14 when it is bent at inradius R.

Even if flexible tube assembly 10 arranged to satisfy inequality (1) is bent at an inradius of 30 mm required for a practical application, coils of belt-like plate 22 of helical tube 14 are not brought into contact with each other. Therefore, flexible tube assembly 10 can be easily bent. According to this effect, even when flexible tube assembly 10 is inserted into a body cavity where flexible tube assembly 10 is required to be bent at a small radius of curvature, e.g., a duodenum, pain can be prevented from being caused to the side of the patient. In addition, this can prevent portions of net tube 18 from being inserted in gaps 16 of helical tube 14.

A second embodiment of the present invention will be described with reference to FIG. 5. The fundamental structure of the second embodiment is substantially the same as that of the first embodiment. Therefore, the same reference numerals in the second embodiment denote the same parts as in the first embodiment, and a description thereof will be omitted.

Figure 5:
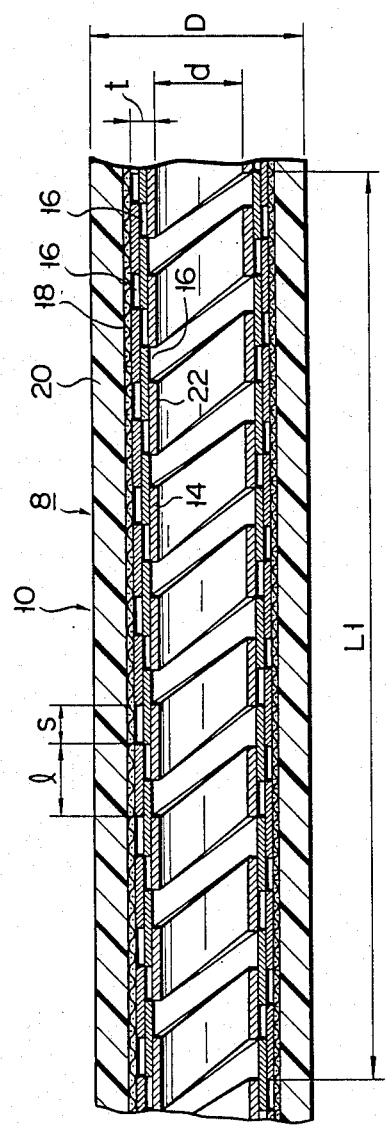
FIG. 5 is a longitudinal view of a flexible tube assembly to a second embodiment of the present invention.

Referring to FIG. 5, helical tube 14 is formed into a three-layer structure having three concentrical layers. Helical tube 14 is designed such that gaps 16 of the overlapping layers do not overlap each other. In this case, coil width l in the axial direction of the three layers of helical tube 14 and gap 16 formed between adjacent coils of each layer are respectively set to be identical to one another.

Assuming that the width and the gap of belt-like plate 22 of each layer of helical tube 14 are respectively set to be l and s, the thickness and the inner diameter of helical tube 14 as a whole are respectively set to be t and d, and the outer diameter of flexible tube assembly 10 is D, then when flexible tube assembly 10 is in a linear state gap s is formed so as to satisfy the following inequality:

$$3 \geq s \geq l(d/2+t)/(30+D/2-d/2-t) \quad (1)$$

Note that although helical tube 14 described above has the three layers, the present invention is not limited to this arrangement. When two layers or four or more layers are arranged, the same effect as in the first embodiment can be obtained by setting the size corresponding to t in the first embodiment to be the thickness of the overall helical tube in the overlapping state.

A third embodiment of the present invention will be described with reference to FIGS. 6 to 8. The fundamental structure of the third embodiment is substantially the same as that of the first embodiment. Therefore, the same reference numerals in the third embodiment denote the same parts as in the first embodiment, and a description thereof will be omitted.

Figure 6:
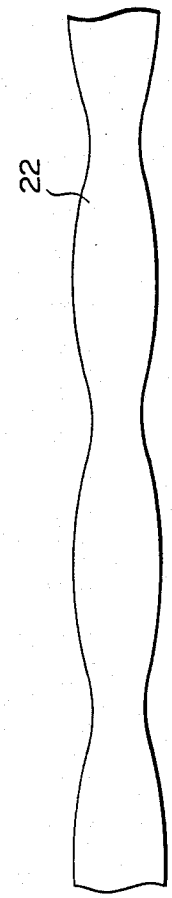
FIGS. 6 and 7 are plan views of a belt-like plate member according to a third embodiment of the present invention.
Figure 7:
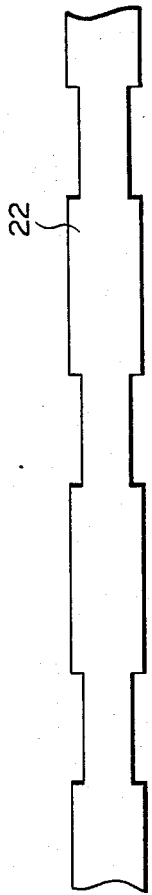

As shown in FIG. 8, belt-like plate 22 formed to have width l with a constant rate of change in the longitudinal direction as shown in FIGS. 6 and 7 is wound such that widths l and gaps s are respectively changed in the axial direction of flexible tube assembly 10.

The sum of widths l of the coils present within arbitrary length L1 of flexible tube assembly 10 is given as:

$$\sum_{i=1}^{n} li \tag{12}$$

The sum of gaps s is represented by:

$$\sum_{i=1}^{n} Si \tag{13}$$

Since n coils of width l are present within length L1, the mean value of widths l is given as:

$$\overline{l} = \left(\sum_{i=1}^{n} li\right)/n \tag{14}$$

Similarly, the mean value of gaps s is given as:

$$\overline{s} = \left(\sum_{i=1}^{n} Si\right)/n \tag{15}$$

The same effect as in the first and second embodiments can be obtained by setting the values of width l and gap s obtained in this manner so as to satisfy inequality (1) in the first embodiment:

$$3 \geq s \geq l(d/2+t)/(30+D/2-d/2-t) \tag{1}$$

A fourth embodiment will be described with reference to FIG. 9. The fundamental structure of the fourth embodiment is substantially the same as that of each of the above-described embodiments. Therefore, the same reference numerals in the fourth embodiment denote the same parts as in each of the embodiments, and a description thereof will be omitted.

Referring to FIG. 9, widths l of coils of belt-like plate 22 of helical tube 14 are constant, however, gaps 16 are formed so as to have varying widths along the axial direction when belt-like plate 22 is helically wound. The flexible tube assembly with the above arrangement is formed in substantially the same manner as in the third embodiment. Since widths l of coils of belt-like plate 22 of helical tube 14 are constant throughout the entire length, the respective values in the fourth embodiment can be represented by the formulas in the third embodiment except for equation (14). That is, the same effect as in each of the above-described embodiments can be obtained by substituting gap s represented by $$\overline{s} = \left(\sum_{i=1}^{n} Si\right)/n \tag{15}$$

for s in inequality (1) and setting the size of each portion so as to satisfy inequality (1).

What is claimed is:

1. A flexible tube assembly for an endoscope, which has outer diameter D, comprising:
a helical tube constituted by a helically wound belt-like member having width l and thickness t, said helical tube having inner diameter d, and gap s being formed between adjacent coils of said belt-like member of said helical tube so as to satisfy the following inequality:

$$3 \geq s \geq l(d/2+t)/(30+D/2-d/2-t) \text{ (mm)};$$

a net tube covering an outer surface of said helical tube; and
an outer sheath covering an outer surface of said net tube.

2. The assembly according to claim 1, wherein said helical tube comprises a multilayer structure having a plurality of layers, each of which has thickness t1, and the sum of thicknesses t1 substantially coincides with thickness t.

3. The assembly according to claim 2, wherein each of said plurality of layers has gap s, and gaps s of the radially adjacent layers do not overlap each other.

4. The assembly according to claim 1, wherein the widths of the coils of said belt-like member are constant throughout a length thereof, and gaps s between the coils are constant throughout a length of said helical tube.

5. The assembly according to claim 1, wherein the coils of said belt-like member have widths li which vary at a predetermined rate throughout a length thereof, width l in said inequality is the mean value of widths li of the coils, said helical tube has gaps Si which also vary along the axial direction thereof, and gap s in said inequality is the mean value of gaps si.

6. The assembly according to claim 1, wherein the widths of the coils of said belt-like member are constant throughout a length thereof, said helical tube has gaps Si which vary along the axial direction thereof, and gap s in said inequality is the mean value of gaps si.

* * * * *